United States Patent
Tamaro

[19]

[11] Patent Number: 5,807,352
[45] Date of Patent: Sep. 15, 1998

[54] SAFETY CAP ASSEMBLY FOR NEEDLES

[76] Inventor: Frank A. Tamaro, 22 Pancake Hollow Dr., Wayne, N.J. 07470

[21] Appl. No.: 858,644

[22] Filed: May 19, 1997

Related U.S. Application Data

[62] Division of Ser. No. 554,037, Nov. 6, 1995, Pat. No. 5,630,803.

[51] Int. Cl.⁶ .................................................. A61M 5/00
[52] U.S. Cl. ........................................ 604/263; 604/192
[58] Field of Search ................................ 604/263, 192, 604/198, 187, 110

[56] References Cited

U.S. PATENT DOCUMENTS

| | | | |
|---|---|---|---|
| 4,139,009 | 2/1979 | Alvarez | 604/198 |
| 5,092,851 | 3/1992 | Ragner | 604/192 |
| 5,242,418 | 9/1993 | Weinstein | 604/192 |
| 5,250,031 | 10/1993 | Kaplan et al. | 604/198 X |
| 5,295,972 | 3/1994 | Mischenko | 604/192 |
| 5,538,508 | 7/1996 | Steyn | 604/263 X |
| 5,685,860 | 11/1997 | Chang et al. | 604/192 |

*Primary Examiner*—John D. Yasko
*Attorney, Agent, or Firm*—W. Patrick Quast, Esq.

[57] ABSTRACT

A safety needle cap assembly for needles is described. In place of the usual safety cap which requires a doctor, dentist or nurse to manually place it in position on a used syringe needle, the safety needle cap assembly of the invention automatically caps the used needle the instant the needle is withdrawn from the patient. An elastic sheath or spring attached to a safety needle cap is kept under tension, retracting the cap and allowing the needle tip to be exposed. Once used and removed from the patient, the elastic tension is released, causing the safety needle cap to snap over the used needle tip automatically, without any operator assistance. The design of the safety needle cap assembly as described virtually preclude accidental re-emergence of the used needle tip during disposal of the needle-cap assembly.

15 Claims, 10 Drawing Sheets

SAFETY CAP ASSEMBLY FOR NEEDLES

This is a divisional application based on the application bearing application Ser. No. 08/554,037 filed Nov. 6, 1995, now U.S. Pat. No. 5,630,803.

BACKGROUND

This invention relates to safety cap assemblies for needles, and in particular, safety cap assemblies for needles used in health-care related procedures.

Needles are, of course, employed in a wide variety of dental and medical procedures, including giving vaccines to patients, the injection of antibiotics, anesthetics, medicines, etc., the drawing of blood samples, intravenous feedings, and so on. Virtually all of these procedures subject medical personnel to the dangers of accidental sticking of the needle into a portion of their own bodies. The danger to the medical professional is primarily due to the possibility of accidentally injecting him or herself with an infectious pathogen derived from the patient after an injection has been delivered to the patient. At the present time, one need only mention the dread acronym "AIDS", (Acquired Immune Deficiency Syndrome) to understand the very real fears of the health professional.

Numerous devices have been suggested and employed to alleviate this problem. However, these devices and techniques require the knowledgeable, conscious cooperation of the physician, dentist, or nurse. Any distraction at the moment a used needle should be safety capped can result in a needle remaining uncapped, and hence a danger to anyone who might come in contact with it. This invention overcomes these disadvantages by providing a safety cap for needles that automatically safety caps the needle at the precise moment the needle is withdrawn from the patent.

The primary object of this invention is to provide a safety cap assembly for needles which automatically safety caps the needle at the moment the needle is withdrawn from the patient, thereby significantly reducing the posssibility of accidental injection.

A further object of the invention is to provide for automatic safety capping of used needles without the requirement of any operator attention.

An additional object of the invention is to provide for automatic safety capping of used needles without the requirement of any operator manipulation to accomplish this safety capping.

Still another object is to provide an automatic safety cap assembly for needles which is light in weight and inexpensive to manufacture.

An additional object of the invention, is to provide an automatic safety cap assembly that cannot inadvertently expose a used needle.

Another object of the invention is to provide an automatic safety cap assembly for virtually any length and gauge of needle.

SUMMARY

These and other objects are obtained in the instant invention of a safety needle cap for needles used in health-care related procedures.

Syringes, medicine delivery systeis, etc. (hereinafter referred to as a "system") are supplied to the medical professional in a variety of ways. They may be made of glass or plastic, with attached, or to be attached needles usually being fabricated in metal, often stainless steel. A system may be supplied filled with appropriate medications, etc., or empty, depending upon the use to be employed. In any case, when a system combined with a needle is being used, the needle is connected to the base of the system by means of an enlarged structure (relative to the diameter of the needle itself) which is either a structural part of the needle, or the system to which the needle is affixed. This enlarged structure which connects the needle to the system, providing a conduit within this structure for fluid flow between the needle and the syringe, is commonly referred to as the needle "hub".

I have found that a safety cap means and an elastic sheath means combination can be fabricated so as to be put in place on virtually any needle assembly, including needle-hub assemblies and individual needles packaged in their own sterile environment. And, of course, the safety cap-elastic sheath assembly combination can be supplied already in place on systems with needles previously connected. The safety cap means of the invention consists essentially of a cap, which can be fabricated in metal or preferably economically molded in a suitable plastic such as, for example, polycarbonate, or any material, which is impenetrable for the particular gauge needle to be enclosed. The elastic sheath means attached to the safety cap means can be fabricated in a variety of resilient materials, such as for example, latex or natural rubber, plastic elastomers, or even plastic or metal springs. By the term "elastic", it is meant a material or structure which is capable of being stretched or compressed, and which, upon release of the stretching or compressing forces, returns substantially to its original shape.

In a first version of the invention to be described, one end of a latex rubber sleeve is attached over the needle hub, while at the other end of the sleeve, a safety needle cap is attached. The safety needle cap can be in a variety of shapes and sizes, a tubular shape being considered practical. This tubular shaped cap is completely open at one end and is connected to the elastic latex sleeve. The other end of the cap is closed except for an opening just large enough to accommodate passage of the particular gauge needle being used. The safety needle cap is attached to the sleeve so that the needle opening at the end of the cap is sufficiently misaligned from axial alignment with the needle, when the latex sleeve is not being compressed, so as to preclude accidental, re entry of the needle through the hole.

In this embodiment, to use the system, the operator would manually position the safety cap so that its opening is in axial alignment with the needle. He would then push the needle through the opening in the cap- the elastic, latex sleeve now being compressed and put under tension by this action of the operator. Depending on the inherent resilience of the elastomeric material employed, axially extending slits, if necessary, running partially along the length of the latex sheath, can facilitate this compression of the sheath. With the needle now exposed, the health professional can now proceed and insert the needle into the patient. The safety needle cap now is in contact with the patient, as for example, the arm of the patient, the cap simply riding back over the needle as the sheath is further contracted by the force applied by the health professional in inserting the needle to the required depth. After the injection, the operator simply withdraws the needle from the patient without the necessity of any thought being given to the safety needle cap. The instant the needle is free of the patient, the elastic tension in the compressed latex sheath is released, causing the safety cap to snap back to its original, off-axis or quiescent position. The needle tip is now safely contained within the needle cap where, of course, it cannot, inadvertently reenter the cap opening. The enclosed needle-hub combination can now be safely disposed of by a health professional, or technician, without any danger of accidentally causing the tip of the needle to protrude from the cap. The entire capping procedure is accomplished automatically, and without reference to the alertness or lack thereof of the operator.

Additional conveniences can be added to the above described device and procedure. For example, in a second version to be described, the safety needle cap-elastic sheath assembly can be supplied with a safety needle assembly enclosure having slots along its length to accommodate oppositely positioned projecting arms affixed to the safety needle cap. In this version, the cap and sheath means and needle would be supplied enclosed within this needle assembly enclosure. This is done with or without the assembly already in place on a system. The projecting arms on the safety needle cap would project through the slots within the safety needle assembly enclosure, the needle is in axial alignment with the needle opening within the cap, the tip of the needle now protruding through this needle opening. In this manner, the device is supplied in a ready-to-operate configuration. To use this version of the invention, the operator places his or her fingers on the projecting arms of the safety needle cap, removes the safety needle assembly enclosure, and proceeds as described in the first version of the invention with the injection. Again, after the needle is removed from the patient, the safety needle cap automatically snaps back to an off-axis position where the cap opening is out of axial alignment position with the needle, so that it is safely captured within the cap.

Two basic designs for the safety cap are disclosed. The first is relatively simple and includes a front face portion including an axially disposed, needle hole of sufficient size so as to accommodate the needle gauge employed. As described, the tubular cap includes cylindrical sidewall means that connects to the elastic sheath means. The sidewall means as assembled to the elastic sheath means extends backwards, in the direction of the needle hub, a sufficient distance so that the needle tip is captured within the volume defined by said front face portion and the distal end of the sidewall.

A second cap design includes a front face portion wherein the needle opening comprises a frusto-conically shaped opening, including a smaller opening on the interior surface of said front face portion and a larger opening on the exterior surface of said face portion. A second, rearwardly disposed face portion includes a second opening and a tubular extension extending rearwardly therefrom, the axis of the second opening and tubular extension being offset from the axis of the openings in the front face portion. This axis offset feature leverages the safety cap, in relation to the needle, so that when the elastic sheath means is in its released, quiescent disposition, the axis of the needle is offset from the axis of the opening in the front face portion of the cap.

The frusto-conical opening in the front face portion is adaptable to be able to retain gauze or similar material to capture and absorb body fluids as the needle, after use, is enveloped within the cap volume defined by the front face portion and sidewalls.

Additional safety enhancing features for use with the cap of either design are disclosed. These include a flap member, hingedly connected to the cap sidewall and disposed in relation to the needle to close off the opening in the front face portion after the device is released from the compressed, sheath means, position. Alternately, the area in the vicinity of the juncture of the sidewall and face portion can be packed with styrofoam or similar material which will capture the needle tip in the sheath means-released position.

In a third version of the invention to be described, the elastic sheath means can be in the form of a metal or plastic spring. The purpose of this spring type of elastic sheath means is the same as for the previous two versions, i.e., to maintain the safety cap in a position so that it will automatically snap back over the needle, with the needle opening within the cap out of alignment with the axial alignment of the needle, after the needle has been withdrawn from the patient. The spring can be enclosed in its own fabric sheath so as to facilitate its connection to the safety cap and needle hub.

A further embodiment depicts the safety cap configured in an "elbow" form. In this version the axial misalignment as is necessary between the cap and the needle in the relaxed, quiescent state is inherent in the cap design.

As will be more fully discussed, the structure of the safety needle cap assembly of the invention can have further modifications to virtually rule out any possibility of inadvertently repositioning the safety needle cap after use in a way that would permit the tip of the needle to re-emerge from the needle opening within the cap. Obviously, on all versions cited above, a sterile safety package, such as a safety foil, can be provided to enclose any described safety needle cap means and elastic sheath means assembly as supplied with or without needles and syringes.

BRIEF DESCRIPTION OF THE DRAWINGS

FIGS. 10, 11(*a*), 11(*b*), 12(*a*), 12(*b*) depict in elevational views a modification to the safety cap feature of the invention.

FIGS. 14(*a*) and 14(*b*) depict in front elevational and side, sectional elevational views the details of one embodiment of the safety cap feature of the invention.

FIG. 15 is a partial, elevational view depicting a further embodiment of the safety cap which is formed in an elbow configuration to accommodate the purposes of the invention.

DETAILED DESCRIPTION

As noted above, the present invention has broad application. For purposes of illustration only, the needle system to be described hereinafter will focus on the syringe system which includes a syringe barrel and plunger. The needle-hub in this system can be formed as part of the barrel or be separate therefrom and which, together with the needle, inserted typically into an opening in the syringe barrel.

Figure 1:
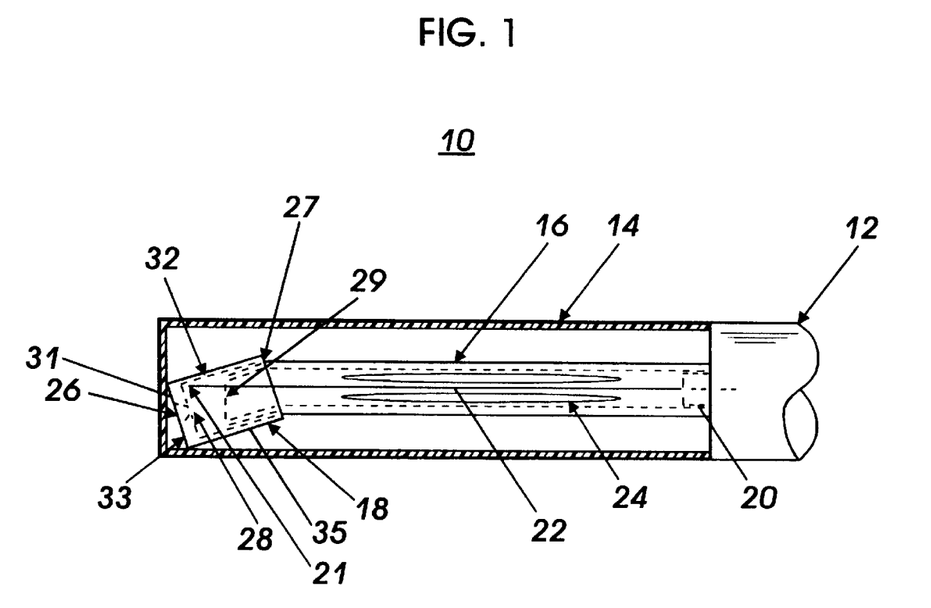
FIG. 1 is an elevational, sectional view of one version of the safety needle cap assembly of the invention.

Turning now to the drawings wherein similar structures, having identical functions, are denoted with the same numerals, FIG. 1 illustrates a complete first version 10 of the safety needle cap assembly of the invention. A syringe 12 is shown with an attached needle 22. The needle 22 is shown enclosed within an elastic sheath means 16, the elastic sheath means being connected at one end to the hub 20 of the needle, and at its other end to a safety needle cap 18. The elastic sheath means can be affixed to the needle hub and safety cap by any convenient means, such as with suitable adhesives, clips (not shown), etc. Where the elastic sheath is formed of an elastomeric material such as latex, the connection can be; made by any suitable means including a frictional fit between the two pieces. The elastic sheath means 16 can be fabricated in a variety of suitable elastomers, e.g. latex rubbers, capable of being easily compressed under tension, and including a good "memory" so as to enable the elastic sheath means to return to its original shape when the tension is released. Other resilient means, for example, a spring, can be employed as the elastic sheath means as will be more fully described and illustrated in FIGS. 6, 6A and 7.

The safety needle cap 18 itself can be fabricated out of a number of hard materials, which will be impenetrable to the needle tip, for example, a clear plastic such as polycarbonate. The shape and size of the safety needle cap can vary depending on applications and design preferences, a tubular shape being suitable for some applications as depicted in FIG. 1. See also FIG. 15 and the attending description.

The tubular shaped safety needle cap is shown fully open 27 at one end for attachment to the elastic sheath 16. As is the case with the needle hub, the other end of the elastic sheath 29 can be attached to the safety needle cap by any convenient means, such as with a suitable adhesive, clips (not shown), frictional fit, etc. The other end of the safety needle cap is closed except for an interior opening 28 within the cap of just sufficient diameter as to permit the passage of the syringe needle 22 through this opening. As will be more fully illustrated and explained, this is an important feature of the invention. It virtually precludes the possibility of inadvertent, re-emergence of the tip 21 of the needle after the needle 22 has been used.

Figures 14A, 14B, 15:
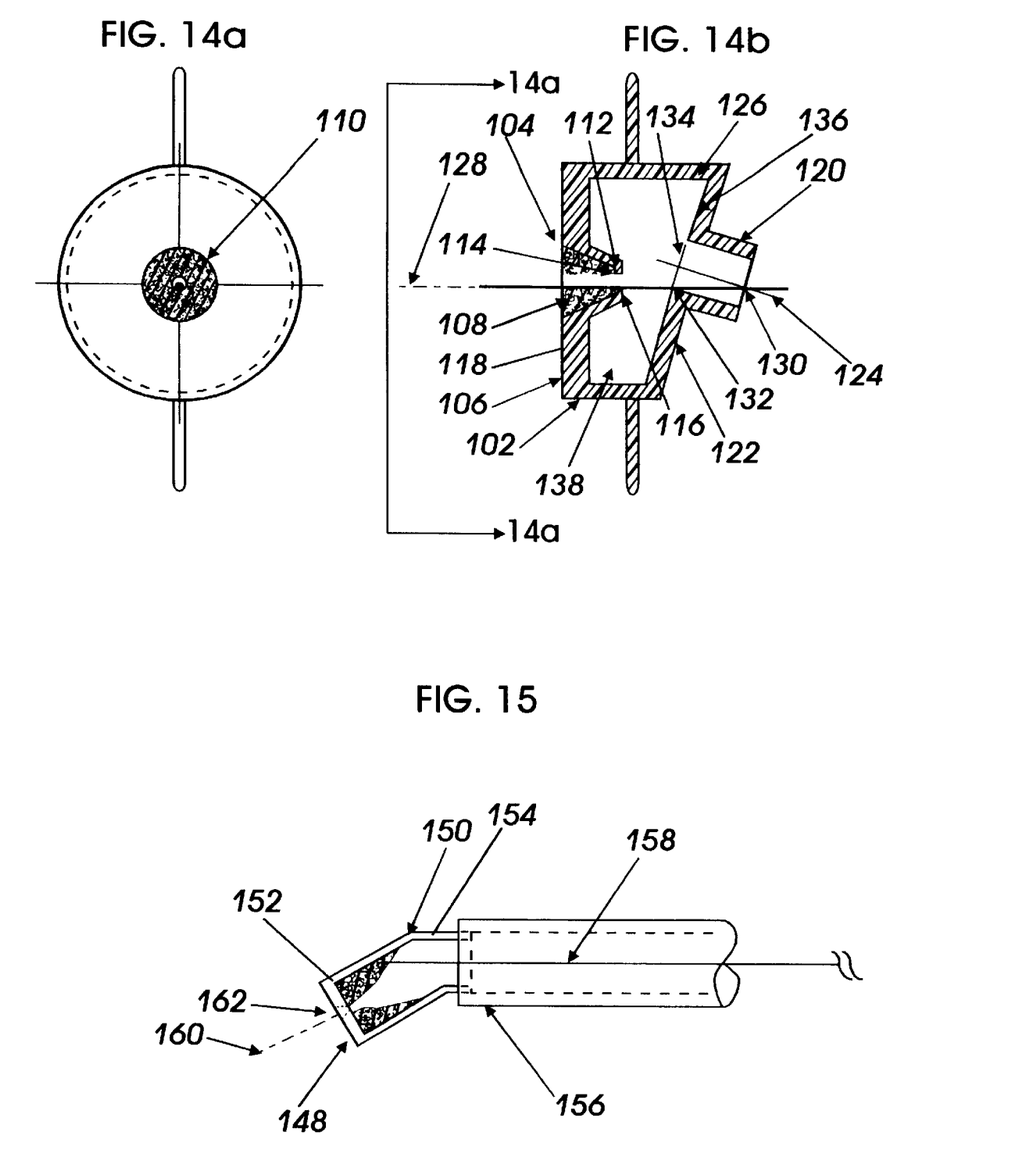

The exterior portion 26 of the interior cap opening 28 is an enlarged frusto-conical shape. It precludes body fluids on the needle from contacting the surface 31 of face portion 33. Gauze or other absorbent mesh work, (see FIG. 14(*a*) and FIG. 14(*b*)), can be secured within the frusto-conically shaped opening to absorp any remaining body fluids on the exterior of the needle as the needle withdraws within the cap after use.

The safety needle cap 18 is affixed to the end of the elastic sheath means. The length of the sheath means between its points of attachment to the cap 18 and the hub 20 is such that the needle tip is enclosed in the volume defined by the face/portion of the cap 33 and the sidewall 35 when the sheath is in its released condition, i.e. not under compression forces. In this relaxed state, the needle opening 28 within the cap is offset from the axial alignment of the syringe 12 and attached syringe needle 22. This arrangement positions the tip 21 of the needle along the upper wall 32 of the tubular side wall of the cap. The elastic sheath means is shown as a tube of latex rubber having slits 24, if necessary, along a portion of the length of the elastic sheath so as to facilitate compressing the sheath when required. The slits can also facilitate a "drooping" of the cap end of the sheath when the system is in the released condition. Where elastomeric material is used, the requirement for slits will depend in part on the gauge, thickness, density, etc. of the material. The entire safety needle cap 18, elastic sheath 16 and syringe needle 22, are shown enclosed in a sterile enclosure 14, which is removed at an appropriate time before use.

Figure 2:
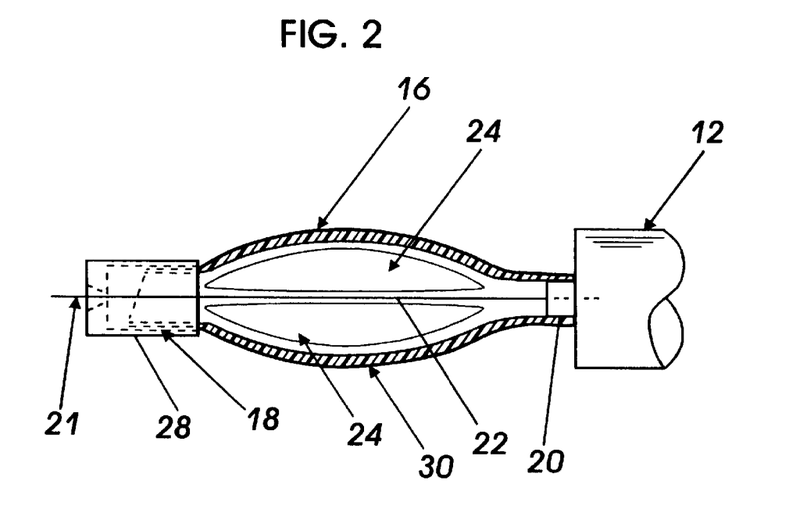
FIG. 2 is an elevational, partial sectional view of the version of the safety needle cap assembly of FIG. 1, illustrating the device ready for use.

FIG. 2 illustrates the version of the invention depicted in FIG. 1, now ready to be utilized with a patient. The sterile metal foil 14 has been removed, and the safety needle cap 18 has been manually moved (not shown) so that the needle opening 28 in the cap is in axial alignment with the hypodermic needle 22, the cap being moved longitudinally along the axis alignment with the needle, causing the elastic sheath 16 to be compressed 30 and therefore under tension, while at the same time exposing the tip 21 of the needle 22. With the hypodermic needle 22 in this position, the needle can now be inserted into the patient to perform the required medical procedure.

Figure 3:
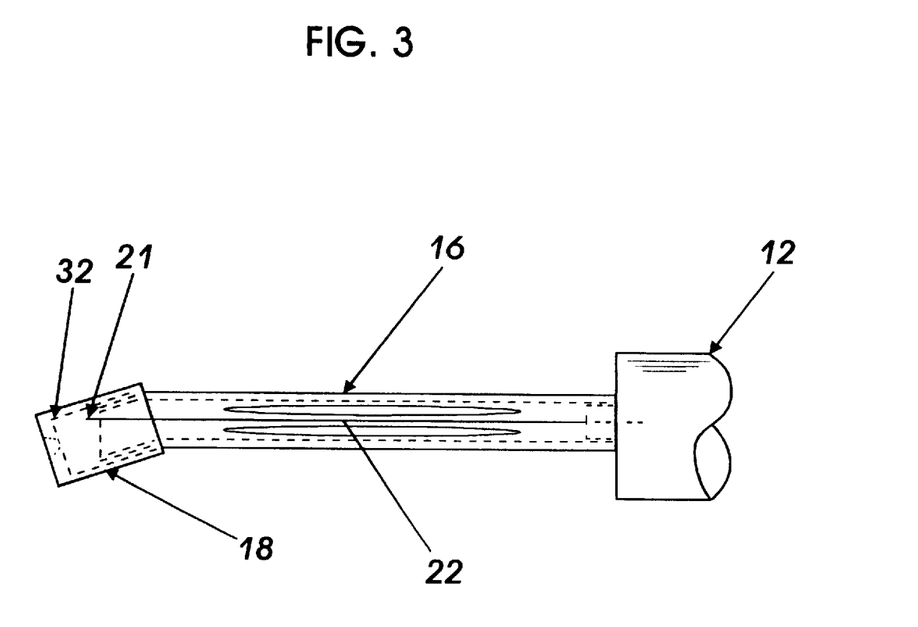
FIG. 3 is an elevational view of the device shown in FIGS. 1 and 2, illustrating the position of the safety needle cap after use.

FIG. 3 illustrates the version of the invention depicted in FIGS. 1 and 2 after the needle has been withdrawn from the patient. This procedure is best understood from FIGS. 8 and 9. The moment the needle is withdrawn from the patient, the elastic tension within the elastic sheath 16 is released which causes the safety needle cap 18 to snap back into its original position. In returning to its original position, the hypodermic needle is caused to be withdrawn to a position within the cap, with the tip 21 of the needle now harmlessly in contact with the inner surface of the upper wall 32 of the safety needle cap 18. The syringe 12 and needle 22 combination, including the safety needle cap 18 and elastic sheath 16, can now be disposed of safely. It is to be noted that the securing of the now potentially dangerous hypodermic needle within the safety needle cap of the invention is accomplished without any manual manipulations by the health professional, or even active consciousness of performing this often extremely important safety procedure.

Figure 4:
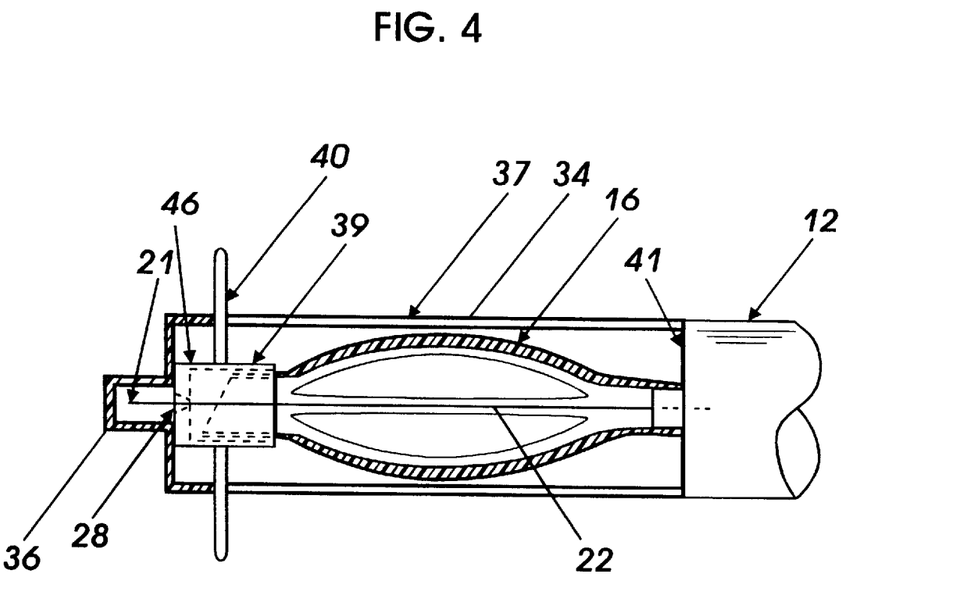
FIG. 4 is an elevational, partial sectional view of a version of the invention, showing a safety needle cap assembly enclosure and modified safety needle cap positioning the needle in ready for use, axial alignment with the needle opening within the cap.
Figure 4A:
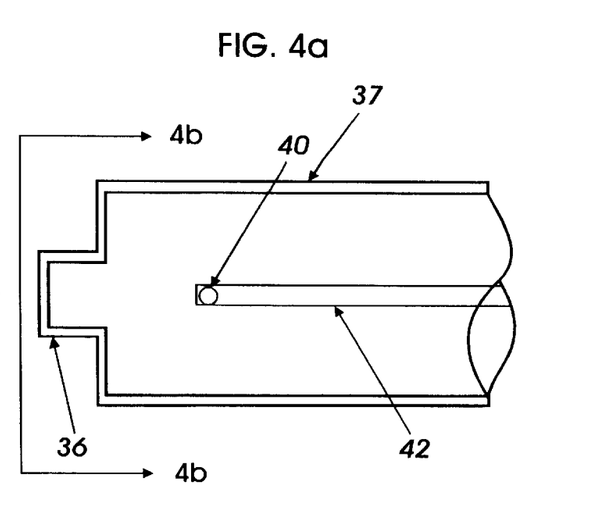
FIG. 4A is a top plan view of the safety needle cap assembly enclosure and syringe depicted in FIG. 4.
Figure 4B:
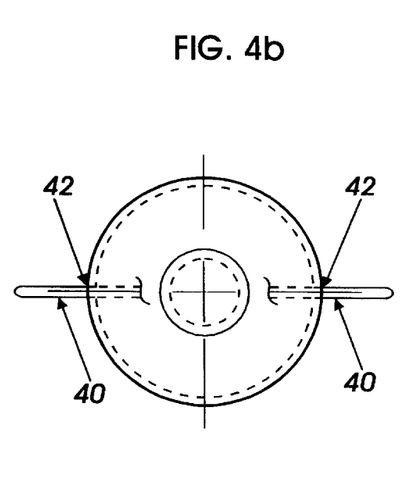
FIG. 4B is a view of the cap assembly of FIG. 4A, taken along lines 4B—4B in that view.

FIG. 4 illustrates a second version of the invention in which a safety needle enclosure assembly 37 cooperates with a modified safety needle cap 39. The modified safety needle cap 39 includes arms 40 attached to and projecting radially outward from the side wall 46 of the modified cap. The attached arms 40 project through slots 42 in the safety needle enclosure assembly 37 (FIG. 4A). The axial length of the enclosure assembly 37 and length of slots 42 are such, that, when the assembly 37 and sheath-cap combination 16-39 is in place on the syringe-needle combination, with the one end of the sheath means secured to the needle hub 20, the arms 40 cooperate with the closed ends of slots 42 to maintain the elastic sheath in a contracted condition under elastic tension. The safety needle enclosure assembly 37 itself can be fabricated in a variety of plastic materials. The safety needle enclosure assembly 37 can have a smaller diameter tubular extension 36 sealed at one end, forming a safety cover for the now exposed tip 21 of the needle. The smaller diameter tubular extension 36 is confluent with a larger diameter tubular extension 34. The open end of the latter contacts the syringe barrel at surface 41 when the assembly-cap-sheath combination, 37-39-16, are in place.

The enclosure 37 including its length and the relative diameter of tubular extension 36, can be designed so that the outside surface of the face portion of cap 39 (corresponding to surface 31—see FIG. 1) contacts the interior surface of the vertical section (as seen in FIG. 4) disposed between the tubular extensions 34 and 36 and before arms 40 ever reach the closed ends of the slots. This design, alternately, can maintain the safety needle cap assembly in a ready condition.

To use the device illustrated in FIGS. 4 and 4A, once the sheath is connected to the hub 20, the operator would grasp the arms 40 extending through the slots 42 in the safety needle enclosure assembly with his or her fingers, then pull the safety needle enclosure 37 off from its contact with the syringe barrel with his or her free hand. With the tip 21 of the needle 22 now exposed and properly aligned, the operator can now proceed with the medical procedure.

Figure 5:
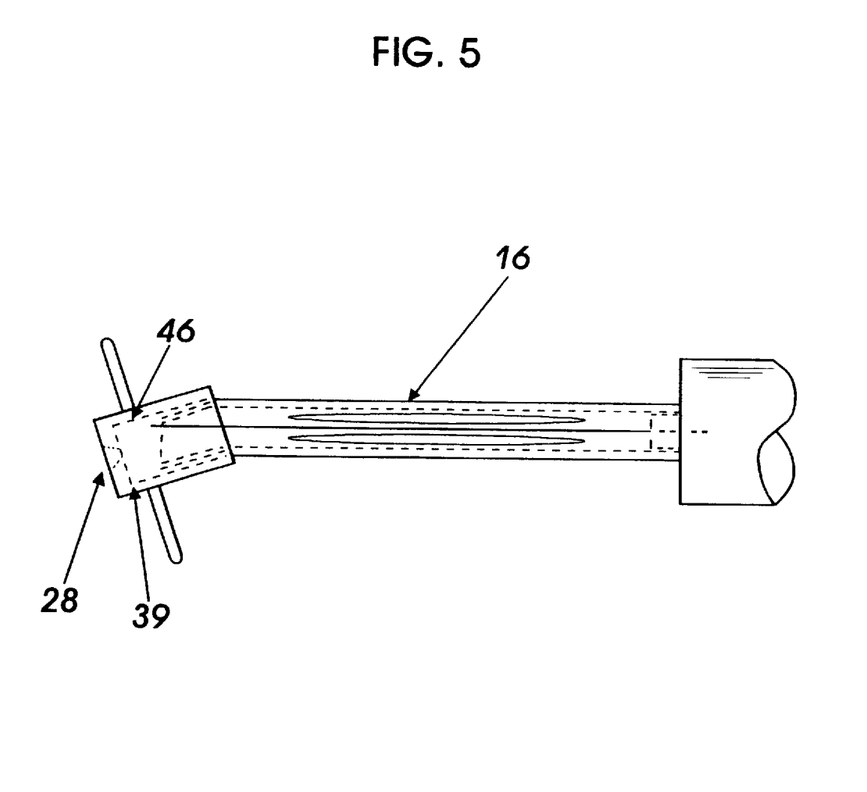
FIG. 5 is an elevational view of the invention depicted in FIG. 4, illustrating the position of the safety needle cap after use.

As shown in FIG. 5, after the needle is withdrawn from the patient, the elastic tension is in the elastic sheath 16, which causes the modified safety needle cap 39 to move forward to a position where it encloses the needle tip, the tip of the needle now resting within the cap on the inside surface 46 of the side wall.

Figure 6:
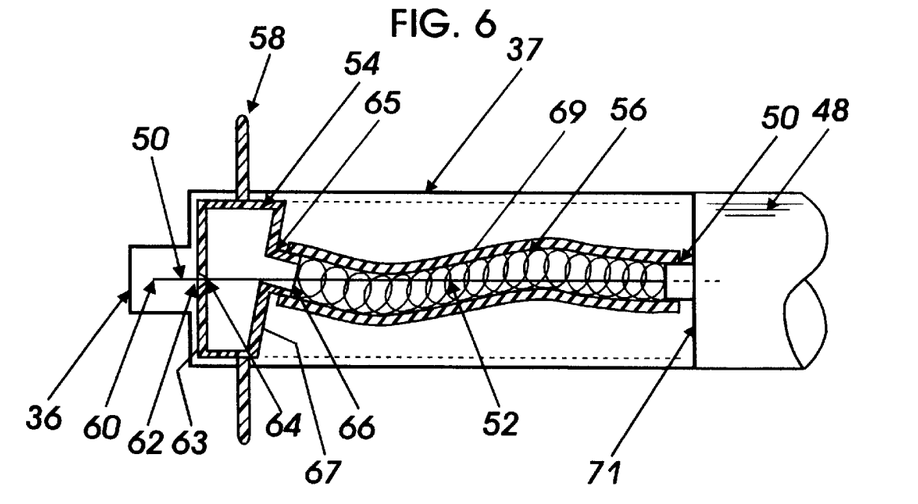
FIG. 6 is an elevational, partial sectional view of a version of the invention which employs a spring for the elastic sheath means, and depicts a second embodiment of the safety needle cap means.
Figure 6A:
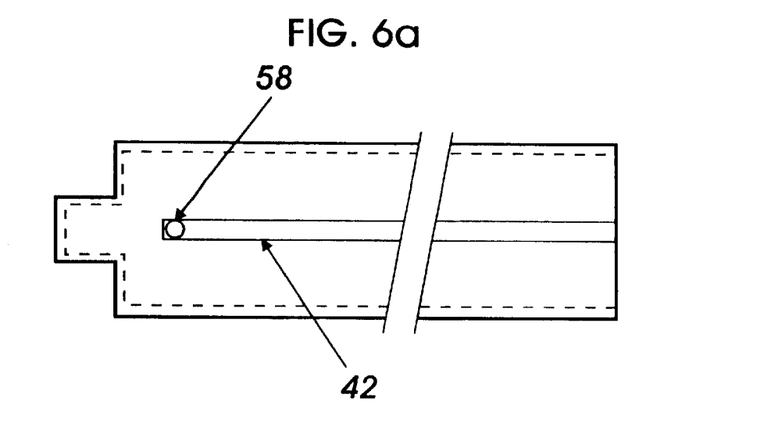
FIG. 6A is a top plan view of a part of the safety needle cap assembly enclosure and syringe depicted in FIG. 6.
Figure 7:
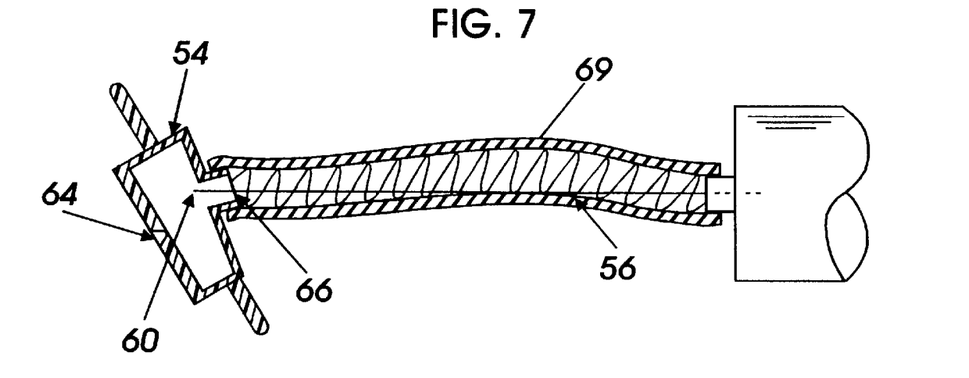
FIG. 7 is an elevational view of the invention depicted in FIG. 6, showing the position of the safety needle cap after use.

In FIGS. 6, 6A and 7, a further version of the invention is illustrated depicting the use of a spring 56 as the elastic sheath means, and illustrating a further modified safety needle cap 54. As described above for FIGS. 4 and 4A a safety needle enclosure assembly 37 encloses the further modified cap 54 and spring elastic sheath 56. One or more arms 58 on the further modified cap project through matching slots 42 in the safety needle enclosure assembly, thereby putting compression tension on the spring 56. Needle 50 is aligned with rear opening 66. The needle is axially aligned with a smaller internal needle opening 64 and a larger, exterior frusto-conical needle opening 62 in a front face portion 63 of cap 54 so that the needle extends through the cap with the tip of the needle 60 now exposed beyond the cap 54, but protected by the tubular extension 36 of the safety needle enclosure assembly 37. The principal modification shown to the cap 54 is that, instead of having a fully opened rear portion of the cap as described in FIGS. 1–5, the rear portion of the cap is substantially closed, by a back face portion 67 which includes a tubular extension 65 having an opening 66. One end of the spring 56 is attached to this tapered tube 65 again in any convenient manner, such as adhesively or with a clamp (not shown), with the other end of the spring 56 similarly attached to needle-hub 50. The spring can be enclosed in a sleeve 69 made of compliant material such as nylon or the like, or even an elastomeric material, such as latex. One end of the fabric enclosure is attached to the extension 65 and the other end to needle hub 50. The spring 56 itself can be fabricated in a variety of suitable materials, including metal or plastic.

As can best be seen in FIG. 6, with the arms 58 secured in the slots 42 within the safety needle enclosure assembly 37, and the one end of the assembly 37 in contact with the surface 71 of the syringe 48, the spring 56 is put under elastic tension. The needle 52 enters the cap through the opening 66 in the tubular extension 65 of the cap 54 and is axially aligned with the internal needle opening 64 and external needle cap opening 62, with the tip 60 of the needle now protruding into the smaller diameter portion 36 of the safety needle enclosure assembly 37. Operator manipulations of the arms 58 and removal of the safety needle enclosure assembly 37 now permits direct utilization of the syringe 48 in the delivery of a medical procedure to a patient.

As illustrated in FIG. 7, after the needle is withdrawn from the patient, the spring tension is released, and the tip 60 of the needle now automatically is positioned within the further modified safety needle cap 54. The opening 64 in the front of the cap and the opening 66 at the rear of the cap are now misaligned to a degree that virtually precludes any possibility of accidentally realigning the needle with the opening 64.

Figure 8:
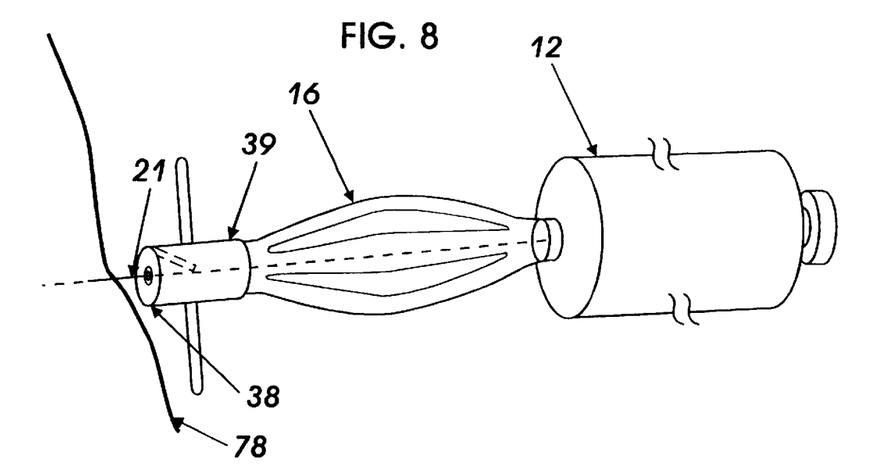
FIG. 8 is a perspective view of one version of the invention as being used to deliver an injection to the arm of a patient.
Figure 9:
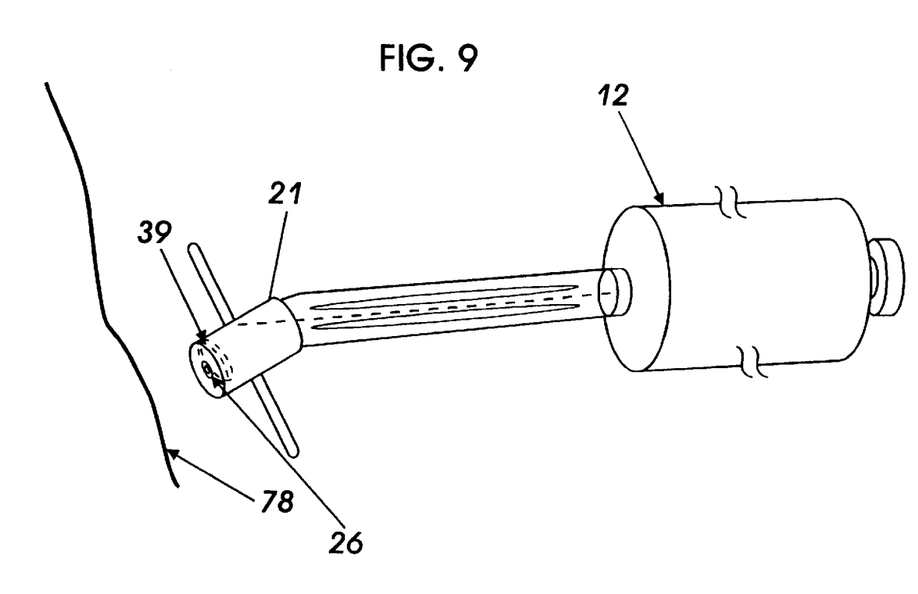
FIG. 9 illustrates the version of the invention as depicted in FIG. 8 after the needle has been withdrawn from the patient's arm.

FIGS. 8 and 9 illustrate the second version of the invention depicted in FIGS. 4, 4A and 5 in actual use on a patient. The tip 21 of the needle is shown penetrating the skin on the arm 78 of a patient with the lower bottom edge 38 of the tubular shaped modified safety needle cap 39 in contact with the skin. This serves to aid in maintaining the cap in a withdrawn position, thus sustaining the tension in the elastic sheath means 16 while a medical procedure is in progress. Once the procedure is completed and the needle withdrawn, FIG. 9, the safety needle cap of the invention snaps over the tip of the needle, safely enclosing the potentially dangerous needle.

Figure 10:
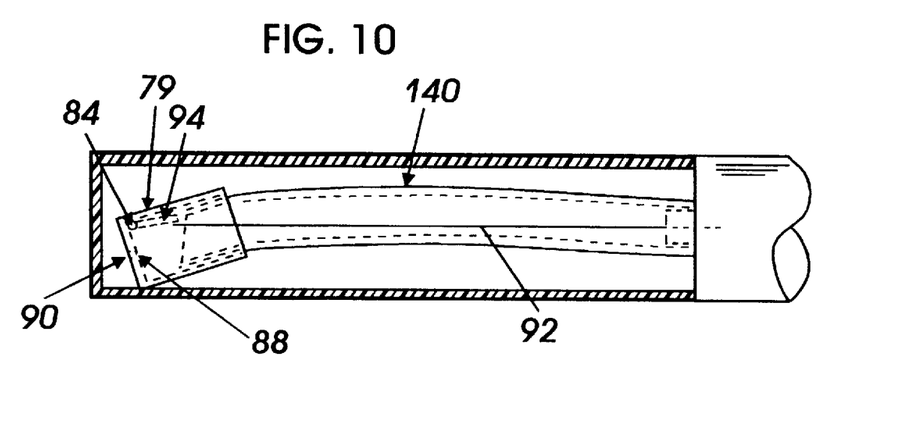
Figure 11A:
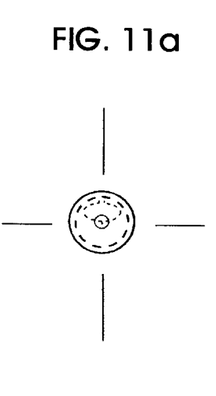
Figure 11B:
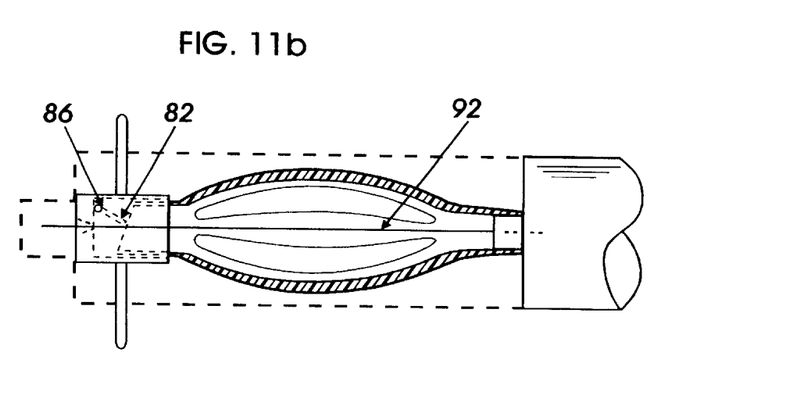
Figure 12A:
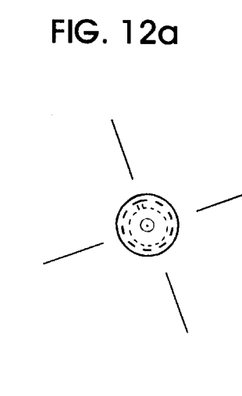
Figure 12B:
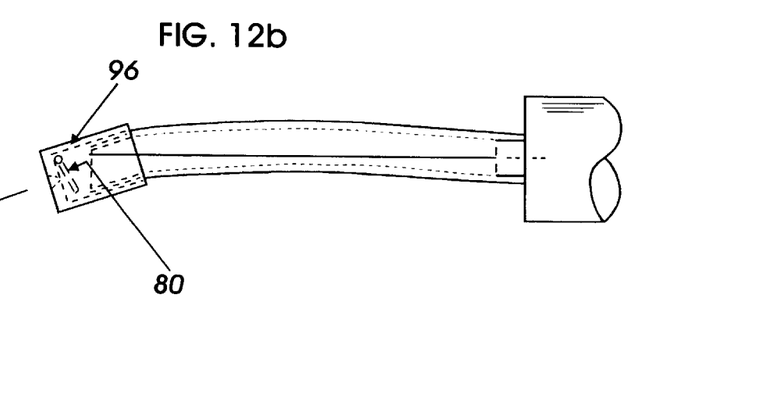

FIGS. 10 through 12 depict supplementary adaptations of the cap member which, if necessary, could be used to ensure the capture of the needle tip after use. FIGS. 10, 11(*a*), (*b*) and 12(*a*) (*b*) illustrate a modified version of the safety cap 79. This modification depicts the incorporation of a closure means 80 including a flap member 82 hinged at 84 to the sidewall 86. The flap member is of sufficient size and hinged to the sidewall in a manner that it closes off the interior side 88 of the opening 90 when the cap-sheath assembly is in its extended position as shown in FIG. 12(*a*) and 12(*b*). FIG. 10 shows the relationship of the flap member 82 to the needle 92 when the cap-sheath assembly is first connected to the needle-syringe assembly. The needle contacts surface 94 of the flap member and captures the flap member 82 between itself and the sidewall 96. This permits the subsequent operation of aligning the needle 92 with the opening 90 in readying the syringe-sheath assembly for use.

FIG. 11(*a*) and 11(*b*) indicate the relationship when the needle is axially aligned and positioned through the opening 90. In this view, the flap member 82 rests on the surface of the needle 92.

The hinged flap member can be included as part of the plastic mold used in forming the cap so that the formed cap product would include the flap member as an integral part. The flap member can be employed with any of the cap members, 18, 39 and 54 described above or as described below in FIG. 15.

Figure 13:
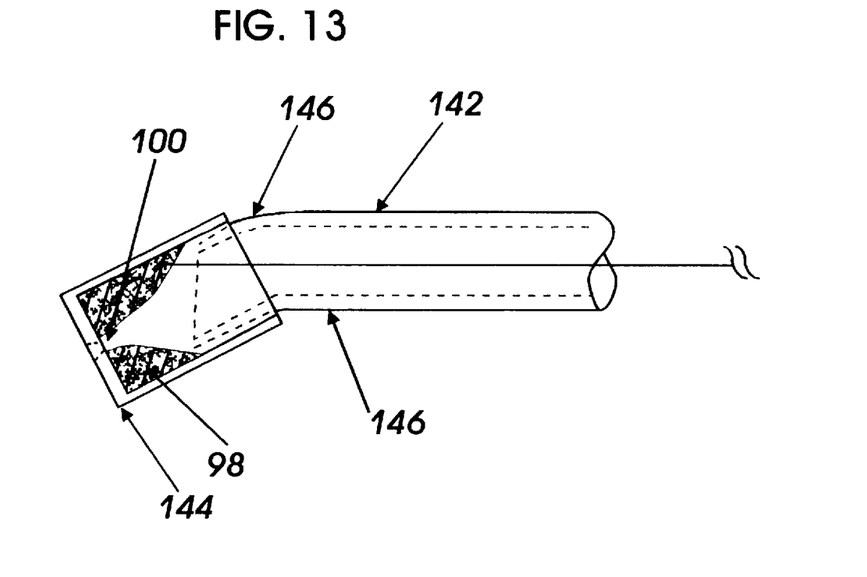
FIG. 13 depicts yet another modification of the safety cap feature of the invention; and, an adaptation of the elastic sheath means portion.

FIG. 13 illustrates the use of an annular ring of styrofoam or similar material 98 to capture and retain the needle point after the medical procedure. The ring is placed inside the cap and secured with appropriate means such as adhesive, at the juncture between the sidewall and interior surface of the face portion. The annular ring as positioned and constructed of course, would permit needle access to opening 100 during set up.

FIGS. 14(a) and 14(b) disclose in close-up a cap member 102 which depicts the preferred construction of the frusto-conical opening 104 in the front face portion 106 and how gauze 108 or other similarly, absorbent material is disposed therein. The gauze is positioned in the frusto-conical opening and secured by a suitable adhesive. Although the cap style depicted is similar to cap 54 above, the configuration of the opening 104 is also appropriate, of course, for the front face portion of any cap configuration including 18 and 39 described earlier or as described below for the cap design of FIG. 15.

The opening 104 includes a first, larger opening 110, which tapers back to a second opening 112, which may be further reduced in size to a third opening 114 by an annular shelf portion 116. The shelf portion can be included in the cap design, if necessary, to facilitate the placement and retention of the gauze 108. Of course, third opening 114 is of sufficient diameter to permit passage therethrough of the particular needle to be used. Preferably the diameter of the first opening 110 is sufficiently large, so that droplets of body fluid which may adhere to the needle as it is withdrawn from the patient do not bridge the space between the needle and the outer surface 118 of the face portion 106.

FIG. 14(b) is also helpful in illustrating an important feature of the style cap depicted (and style 54 of FIG. 6). Tubular extension 120 formed in back face portion 122, is centered on axis 124 which is offset in relation to the axis of the frusto-conical opening 104 on the front face portion. Both before readying the cap-sheath assembly and the needle-syringe assembly prior to use, and after withdrawing the needle from the patient when the sheath means relaxes and the needle tip is captured within the volume defined by the front face portion 106, back face portion 122 and the sidewall 126, the tubular extension 120 serves a useful purpose. The tubular extension 120 and more particularity the angular orientation of back face portion 122 in relation to the front face portion, ensures that the needle is orientated in a direction essentially parallel to axis 124, and necessarily, is, offset to the axis 128 that the needle aligns itself to when it is inserted through the opening 114. In effect, the cap 102 pivots about the needle 130 at point 132 of the opening 134 on the interior surface 136 of the back face portion 122 whenever the needle tip is positioned in the interior volume 138 as defined by the face portions and sidewall. This occurs, again, prior to readying the assembled cap-sheath-needle-syringe assembly and after the relaxed sheath means moves the cap forward, after use, and the needle enter the volume 138, offset from axis 128. This precludes reentry through opening 114.

Finally, referring for the moment to FIGS. 10 and 12(b) assume the sheath means therein depicted, 140, is fabricated from an elastomeric material such as latex. For the particular cap design illustrated and cap design 18 and 39 above, i.e. designs without the back face portion such as 122 in FIG. 14(b), it is of benefit, depending on its thickness and material, that the elastomeric sleeve tends to arc, as depicted, due to the weight of the cap when the needle withdraws into the interior volume of the cap. Thus in this relaxed state the effect of gravity can cause the cap end of the sheath to droop or arc so that the needle opening 100 within the cap is offset from axial alignment with the needle 92. Alternately, the elastomeric sleeve can be formed at manufacture to include the arc. This inherently results in the opening in the cap, 90, being offset to the axis of the needle, thus advancing the purposes of the invention.

FIG. 13 depicts an alternate sheath means 142. The sheath means in this embodiment is fabricated with a suitable bend 146 formed in the material to ensure that opening 100 will be offset from the needle axis when the needle tip is positioned within the cap volume.

In order to provide the offset from the needle axis as required, yet another embodiment as seen in FIG. 15 depicts the cap 148 as fabricated with an angular offset 150 between a front portion 152 and rear portion 154. Here, of necessity, irrespective of the orientation assumed by the sheath means 156 in the relaxed condition, the needle 158 is offset from the axis 160 of the opening 162. The needle is thus precluded from re entering the opening unintendedly.

Thus, it can be seen that a new and economical safety device is provided to health professionals in the utilization of virtually any type of syringe. The safety needle cap-sheath assembly of the invention can be supplied either for field connection to existing syringe and needle assemblies, or, of course, as a complete package including the needle and syringe. In use, the instant invention provides the new and important advantage of safely enclosing a potentially dangerous, used needle, automatically, without any necessity for conscious safety precautions on the part of the health professional.

While the present invention has been disclosed in connection with versions shown and described in detail, various modifications and improvements will become readily apparent to those skilled in the art. Accordingly, the spirit and scope of the present invention is to be limited only by the following claims.

What is claimed is:

1. A safety needle cap assembly for use in combination with a hub portion for holding a needle, said assembly comprising:

(a) a safety needle cap;
(b) an elastic sheath means;
   said elastic sheath means including a first end, said first end connected to said safety needle cap;
   said sheath means including a second end for connecting to the hub portion;
   said safety needle cap having a front face portion, and side wall means connected to said front face portion and extending back from said front face portion a minimum distance to a rear end;
   said front face portion of said safety needle cap having a first opening, larger in diameter than the diameter of the needle; and,
(c) a back face portion disposed along said side wall means a minimum distance back from said front face portion and connected to said side wall,
   said back face portion including a second opening having a second axis, said second axis axially offset from said first axis;
   said safety needle cap being constructed so as to prevent the passage therethrough of the needle other than through said first opening, so that when the needle is attached to the hub portion, and when the needle is positioned within said elastic sheath means with said second end of the said sheath means being connected to the hub portion in a pre-ready condition, and when said cap is moved by an operator so that a first axis of said first opening in said front face portion of said cap is in axial alignment with the axis of the needle, the needle within said cap can now be induced by said operator to pass through said opening in said front face portion of said cap to a ready position, the motion of said cap sliding back over the needle causing said elastic sheath means to be compressed so that when the needle is withdrawn during a procedure involving injecting the needle into a patient, and said compressed elastic sheath means is released, said cap is automatically urged forward by the releasing elastic sheath means over the tip of the needle and beyond to a released condition, said second opening adapted to cooperate with the needle so as to position said safety needle cap in the pre-ready and released conditions, in an orientation, such that said first opening is not axially aligned with the axis of the needle, the minimum distance that said back face portion is disposed along said side wall means and the length of said elastic sheath means in said released condition being sufficient such that the tip of the needle in the pre-ready or released condition of said elastic sheath means is captured within a volume defined by said front face portion and said back face portion.

2. The safety needle cap assembly claimed in claim 1, wherein said first opening is a frusto-conically, shaped opening, the opening on the inside surface of said front face portion being smaller than the opening on the outside surface of said front face portion.

3. The safety needle cap assembly claimed in claim 2, wherein the opening on the outside surface of said front face portion, is of sufficient diameter such that body fluids adhering to said needle after withdrawal from the patient do not bridge the distance between the needle and the outside surface of said front face portion beyond the perimeter of the opening disposed on the outside surface of said front face portion.

4. The safety needle cap assembly claimed in claim 2, wherein an absorbent material is securely disposed in said frusto-conical opening.

5. The safety needle cap assembly claimed in claim 3, wherein an absorbent material is securely disposed in said frusto-conical opening.

6. The safety needle cap assembly claimed in claim 1, wherein said safety needle cap includes at least one arm extending radially outward from the side wall of said cap.

7. The safety needle cap assembly claimed in claim 1, further comprising:

an enclosure assembly, said enclosure assembly disposed to enclose said safety needle cap and said elastic sheath means in said ready condition, said enclosure assembly adapted to cooperate with said safety needle cap, whereby said safety needle cap assembly is maintained in the ready condition.

8. The safety needle cap assembly claimed in claim 6, further comprising:

an enclosure assembly, said enclosure assembly disposed to enclose said safety needle cap and said elastic sheath means in said ready condition, said enclosure assembly including at least one slot, said slot adapted to cooperate with said radially projecting arm, whereby said safety needle cap assembly is maintained in the ready condition.

9. The safety needle cap assembly claimed in claim 1, wherein said elastic sheath means comprises an elastomeric material.

10. The safety needle cap assembly claimed in claim 9, wherein said elastomeric material includes at least one slit whereby the compression of said elastomeric material into the ready condition, is faciliated.

11. The safety needle cap assembly claimed in claim 1, wherein said elastic sheath means includes spring means.

12. The safety needle cap assembly claimed in claim 11, wherein said spring is enclosed in a sleeve of compliant material.

13. The safety needle cap assembly claimed in claim 7, wherein said elastic sheath means comprises an elastomeric material.

14. The safety needle cap assembly claimed in claim 8, wherein said elastic sheath means comprises an elastomeric material.

15. The safety needle cap assembly claimed in claim 1, wherein the second opening in back face portion includes a tubular extension coaxially aligned with said second axis, said tubular extension adapted to cooperate with said needle to offset said needle from said first axis in the pre-ready or released conditions.

* * * * *